(12) United States Patent
Camps et al.

(10) Patent No.: US 6,434,431 B1
(45) Date of Patent: Aug. 13, 2002

(54) INTRAMUSCULAR MEDICAL ELECTRICAL LEAD WITH FIXATION MEMBER

(75) Inventors: Antoine Camps, NJ Eys; Victor Duysens, CP Stein, both of (NL); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/487,787

(22) Filed: Jan. 20, 2000

(51) Int. Cl.[7] .................................................. A61N 1/05
(52) U.S. Cl. ....................................................... 607/132
(58) Field of Search ................................ 607/126–128, 607/130–132, 116, 119; 600/375

(56) References Cited

U.S. PATENT DOCUMENTS

| | | |
|---|---|---|
| 3,474,791 A | 10/1969 | Bentov |
| 3,682,162 A | 8/1972 | Colyer |
| 3,757,790 A | 9/1973 | Herrmann |
| 4,245,643 A | 1/1981 | Benzing, III et al. |
| 4,408,617 A | 10/1983 | Auguste |
| 4,444,207 A | 4/1984 | Robicsek |
| 4,735,205 A | 4/1988 | Chachques et al. |
| 5,300,107 A | 4/1994 | Stokes et al. |
| 5,314,463 A * | 5/1994 | Camps et al. ............... 607/129 |
| 5,423,876 A | 6/1995 | Camps et al. |
| 5,425,751 A | 6/1995 | Baeten et al. |
| 5,755,758 A * | 5/1998 | Woloszko et al. .......... 607/116 |
| 5,792,217 A | 8/1998 | Camps et al. |
| 5,834,051 A | 11/1998 | Woloszko et al. |
| 5,871,528 A | 2/1999 | Camps et al. |
| 5,928,278 A | 7/1999 | Kitschmann |
| 5,938,596 A | 8/1999 | Woloszko et al. |

* cited by examiner

*Primary Examiner*—George R. Evanisko
(74) *Attorney, Agent, or Firm*—Thomas F. Woods; Thomas G. Berry

(57) ABSTRACT

The present invention relates to an intramuscular medical electrical lead, a system for providing electrical stimulation or sensing using such a lead, and methods of implanting, making and using same. The lead includes at least a first fixation member disposed distally or proximally from a sensing or stimulating electrode, and may further include a second fixation member disposed at the opposite end of the electrode form the first fixation member. The fixation members permit the electrode to be reliably and fixedly secured within a patient's muscle tissue at a desired site, and to remain so secured for a predetermined suitable period of time.

2 Claims, 7 Drawing Sheets

INTRAMUSCULAR MEDICAL ELECTRICAL LEAD WITH FIXATION MEMBER

FIELD OF THE INVENTION

The present invention relates to intramuscular electrical medical leads.

BACKGROUND OF THE INVENTION

Surgically implanted medical electrical leads for temporary stimulation of various organs in the human body are well known in the art, some examples of which may be found in the issued U.S. Patents listed in Table 1 below.

TABLE 1

Background Patents

| U.S Pat. No. | Title |
| --- | --- |
| 3,474,791 | Multiple Conductor Electrode |
| 3,682,162 | Combined Electrode and Hypodermic Syringe Needle |
| 3,757,790 | Threshold Analyzer and Stimulator Testing Device with Internal Generator |
| 4,245,643 | Method and Apparatus for Measuring the Ohmic Contact Resistance of an Electrode Attached to Body Tissue |
| 4,408,617 | Apparatus for Detecting the Acupuncture Points on a Patient and for Applying Electrical Stimulating Signals to the Detected Points |
| 4,444,207 | Method of Anchoring a Temporary Cardiac Pacing Lead |
| 4,735,205 | Method and Apparatus Including a Sliding Insulation Lead for Cardiac Assistance |
| 5,300,107 | Universal Tined Myocardial Pacing Lead |
| 5,314,463 | Bipolar Nerve Electrode |
| 5,423,876 | Intramuscular Lead Having Improved Insertion |
| 5,425,751 | Method and Apparatus for Optimum Positioning of a Muscle Stimulating Implant |
| 5,755,758 | Intramuscular Stimulation Lead with Enhanced Infection Resistance |
| 5,792,217 | Temporary Bipolar Heart Wire |
| 5,834,051 | Intramuscular Stimulation Lead with Enhanced Infection Resistance |
| 5,871,528 | Temporary Bipolar Heart Wire |
| 5,928,278 | Defibrillation Electrode |
| 5,938,596 | Medical Electrical Lead |

All patents listed in Table 1 hereinabove are hereby incorporated by reference herein, each in its respective entirety. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously in accordance with the teachings of the present invention.

In respect of known intramuscular medical stimulation leads, sliding members disposed on the lead bodies thereof may act as a source of bacterial infection. See, for example, the '758 patent referenced in Table 1 hereinabove. Additionally, non-conductive polypropolene monofilaments employed in known intramuscular leads have been criticized as being too stiff and difficult to tie into a knot. Moreover, fixation of the aforementioned sliding members to muscle tissue is not always possible. Indeed, such sliding members have a tendency to move after a suture has been applied around the barrel anchor thereof.

Thus, there exists a need to reliably and fixedly implant temporary stimulation leads for intramuscular applications.

SUMMARY OF THE INVENTION

The present invention has certain objects. That is, the present invention provides solutions to problems existing in the prior art. It is an object of the present invention to provide an intramuscular medical electrical lead which may be reliably and quickly affixed to muscle tissue. It is further object of the present invention to provide an intramuscular medical electrical lead which is quickly and easily attached to human muscle tissue. It is a still further object of the present invention to provide an intramuscular medical electrical lead which Various embodiments of the present invention have one or more advantages. More particularly, various embodiments of the intramuscular medical electrical lead of the present invention: (a) reduce the amount of time required to implant an intramuscular lead in muscle tissue; (b) prevent one or more electrodes to be reliably and fixedly implanted within human muscle tissue; (c) reduce patient trauma; (d) reduce the number of puncture sites in the muscle tissue; (e) can be easy to use; (f) attach to external pacemakers, defibrillators, monitoring equipment and other external electrical apparatus quickly, easily, securely and reliably; and (g) increase patient safety owing to shortened implantation times, quicker connection to external stimulation or monitoring equipment, and more reliable fixation to muscle tissue.

Various embodiments of the intramuscular medical electrical lead of the present invention have certain features, including one or more of the following: (a) an intramuscular lead having at least one proximal fixation member; (b) an intramuscular medical electrical lead having at least one distal fixation member; (c) an intramuscular medical electrical lead having proximal and distal fixation members, (d) an intramuscular medical electrical lead having a proximal or distal fixation member, where the fixation member is selected from a group consisting of a trumpet-shaped member, a tined member, and a helical screw; and (e) an intramuscular medical electrical lead having an electrode section which may be elongated or compressed during the implantation procedure.

Other objects, features, advantages and embodiments of the present invention will become apparent upon reading the Detailed Description of the Preferred Embodiments and the Claims.

DETAILED DESCRIPTION OF THE PREFERRED EMBODIMENTS

Figure 1:
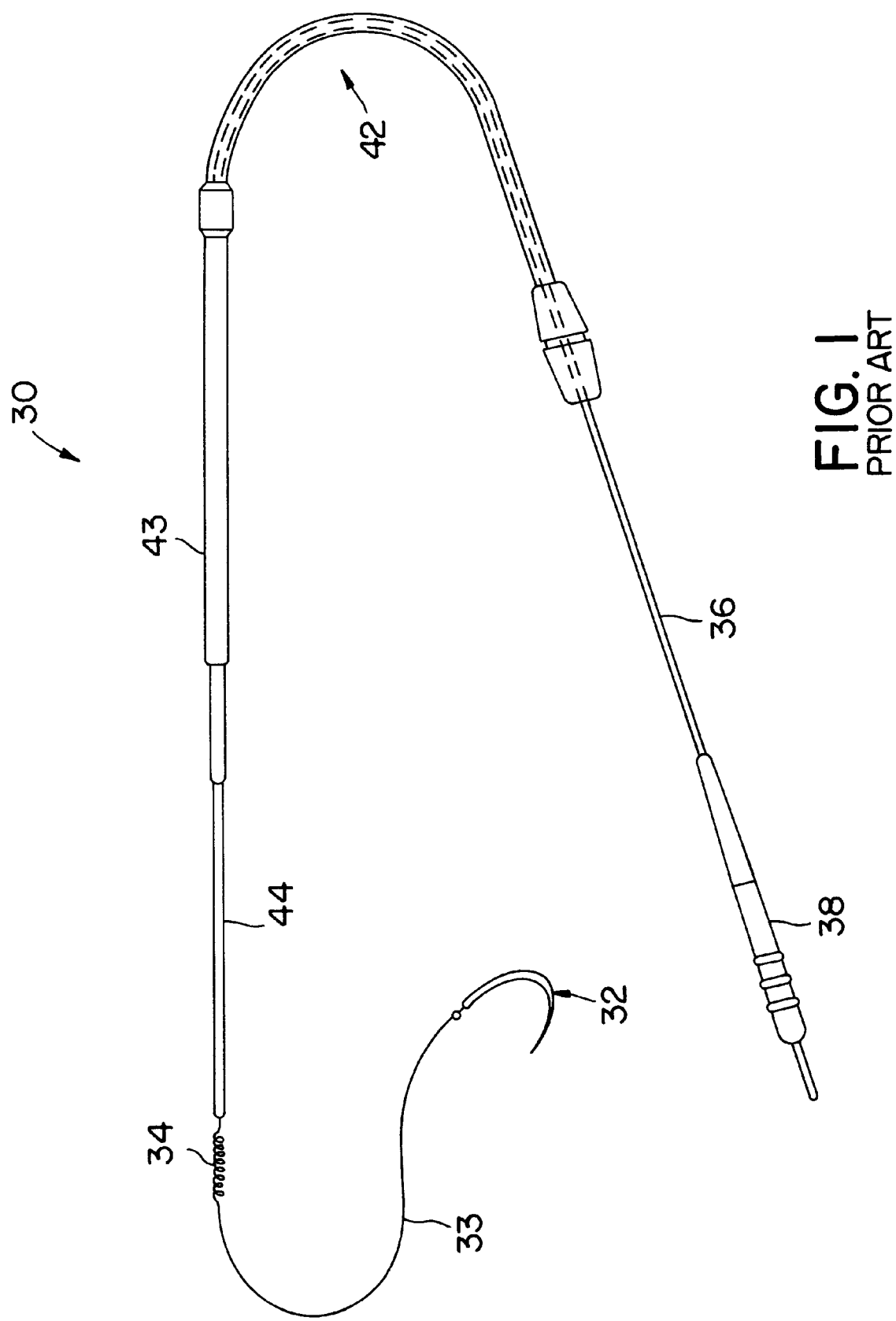
FIG. 1 shows a prior art intramuscular lead.

FIG. 1 shows a prior art intramuscular medical electrical lead disclosed in U.S. Pat. No. 4,735,205 to Chachques et al. entitled "Method and Apparatus for a Sliding Insulation Lead for Cardiac Assistance". In FIG. 1, pulse generator 5 (not shown in FIG. 1) is coupled to intramuscular lead 30 comprising suture needle 32, distal member or line 33, pigtail coil 34, lead body 36, IPG connector 38, slidable insulating tube or sheet 42 and electrode 44. Suture needle is adapted to be drawn through the muscle which is to be electrically stimulated. Electrode 44 is implanted within the desired muscle by being drawn therethrough using line 33 attached to suture needle 32. Needle 32 is first inserted through the muscle and electrode 44 drawn therethrough by means of line 33. Connector 38 is adapted for coupling to one or more output terminals of implantable pulse generator (IPG) 5 after electrode 44 has been appropriately implanted in muscle tissue.

Figure 2:
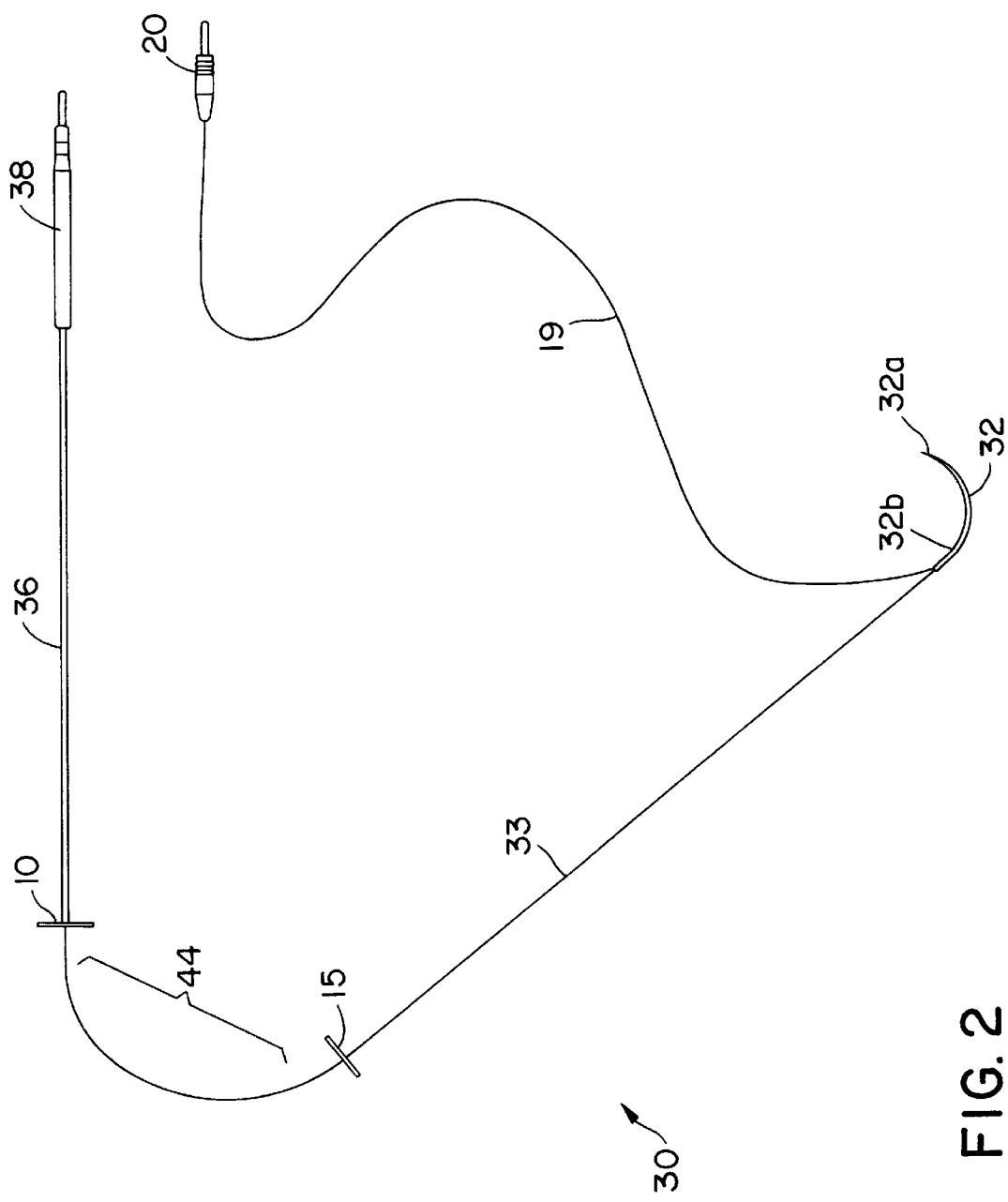
FIG. 2 shows one embodiment of an intramuscular lead of the present invention.

FIG. 2 illustrates one embodiment of an intramuscular medical electrical lead of the present invention. Medical electrical lead 30 in FIG. 2 comprises proximal IPG connector 38, lead body 36, proximal fixation member 10, electrode 44, distal fixation member 15, line 33, needle 32, temporary testing wire 19, and test connector 20. Needle 32 may further comprise pointed electrically conductive tip 32a and portion 32b having electrically insulative material disposed thereover. Note that in various embodiments of the present invention only one fixation disk member 10 or 15 may be present. Fixation member 10 is preferably fixedly attached to lead body 36 and/or electrode 44, while distal fixation member 15 is preferably attached to the distal end of electrode 44 after electrode 44 has been suitably positioned and placed within muscle tissue and needle 32 has been removed by the physician from the distal end of lead 30. In one such embodiment of the present invention, distal fixation member 15 forms a circular disk having a hole disposed through the center thereof through which line 33 is threaded, with fixation member 15 then being slid proximally up line 33 until it engages the distal end of electrode 44 and is snapped or clicked into place thereover for relatively rigid fixation thereto.

Prior to implanting electrode 44, an optimum electrode implantation location may be determined as follows. To determine the best location for muscle implant 44, threshold measurements at various test locations may be carried out on the muscle. One consideration in evaluating such a location is whether a location requires only a low threshold stimulation signal (and hence low energy consumption) to cause muscle contraction. Obviously, locations having the lowest stimulation thresholds are preferred. Another consideration in evaluating a stimulation location is whether stimulation at such a location causes muscle contractions to be large. It is generally preferred that muscle contractions be large. The foregoing two considerations are generally weighed together in determining an optimum electrode location.

In the present invention, an optimal electrode position may be determined by using needle 32, and more particularly needle point 32a, as a test electrode probe. Needle point 32a is placed in contact with various test locations on the surface of a muscle. Temporary conductor or test wire 10 is provided for supplying electrical current to needle 32 from an external pulse generator (not shown). Because needle 32 must be gripped by the surgeon during the testing of prospective implant electrode locations, the outside surface of the proximal gripping portion of needle 32 spaced from sharp muscle-contacting probend 32a thereof may be provided with a suitable insulating coating 32b such as a polyurethane adhesive. Distal end 32a of needle 32 must make electrical contact with the muscle tissue being tested and therefore is not insulated. It will be understood by those skilled in the art that needle 32 need not be coated to be functional.

Use of needle 32 for testing relation of a muscle tissue area is accomplished by gripping the insulated surface 32b thereof and holding the uninsulated contact point area 32a and electrical contact for selected test areas of the muscle tissue. There is a risk of local tissue damage if sharp point 32a of needle 32 penetrates the surface of the muscle. Non-penetrating contact has therefore been found to be preferable to inserting the sharp end of the needle into the tissue.

After testing the various prospective implant locations, determining the optimum location, temporary testing wire 19 is severed adjacent to its attachment point with needle 32. Needle 32 is then employed by the surgeon to penetrate the targeted muscle and permit electrode 44 of lead 30 to be drawn into an optimum position for periodic stimulation.

In a preferred embodiment to the present invention, line 33 is electrically nonconductive and is made of an absorbable or bioabsorbable suture material so that it is eventually absorbed by the muscle tissue after implant. Such materials include DEXON®, VICRYL®, MAXON® and PDS®.

In another embodiment of the present invention, nonconductive line 33 is replaced with a thin conductor wire having an outer insulative coating such as is preferably the case with temporary conductor or test wire 10. Connector 38 is connected to implantable pulse generator 5 (not shown in FIG. 2). Once the optimum electrode stimulation location has been determined, electrode 44 is inserted in the targeted muscle, followed by cutting temporary testing wire 19 at the end located near needle 32. Continuing to refer to FIG. 2, line or member 33 is most preferably a monofilament wire formed of polypropylene. Lead body 36 may comprise any suitable flexible electrical conductor, such as strands of multifilament or twisted stainless steel. Lead body 36 most preferably comprises an electrical conductor that provides a high degree of flexibility and superior mechanical and electrical properties. In preferred embodiments of the present invention the electrical conductor of lead body 36 is covered with an appropriate electrical insulator such as silicone rubber, polyurethane, polyethylene, polypropyleve, polyamide, combinations and mixtures of the foregoing, and other suitable materials. The electrical conductor disposed within lead body 36 is most preferably formed from twisted or helically wound strands of medical grade stainless steel wire. Less preferably, the conductor may be formed of single strands of stainless steel, or of one or more strands of electrically conductive polymeric material.

The insulation disposed over the electrical conductor is most preferably formed of flourinated ethylenepropylene ((FEP), polytetrafluoroethylene (PTFE), or any other suitable medical grade, biocompatible dielectric insulating coating such as co-polymer polytetrafluoroethylene, polyethylene, silastic, neoprene, polypropylene, or polyurethane. Likewise, proximal and distal fixation members 10 and 15 may be formed of the same or similar materials.

Electrode 44 is most preferably formed of a platinum/ iridium alloy, wherein platinum comprises 90 percent of the alloy and iridium comprises 10%. Electrode 44 is mechanically and electrically connected by an electrical conductor disposed within lead body 36 (not shown in the Figures). The electrical conductor, in turn, is attached to the distal end of IPG connector 38. Lead 30 includes current needle 32 for piercing muscle tissue preparatory to drawing electrode 44 within the muscle tissue. The proximal end of curved needle 32 is connected to line or strand 33.

Figure 3:
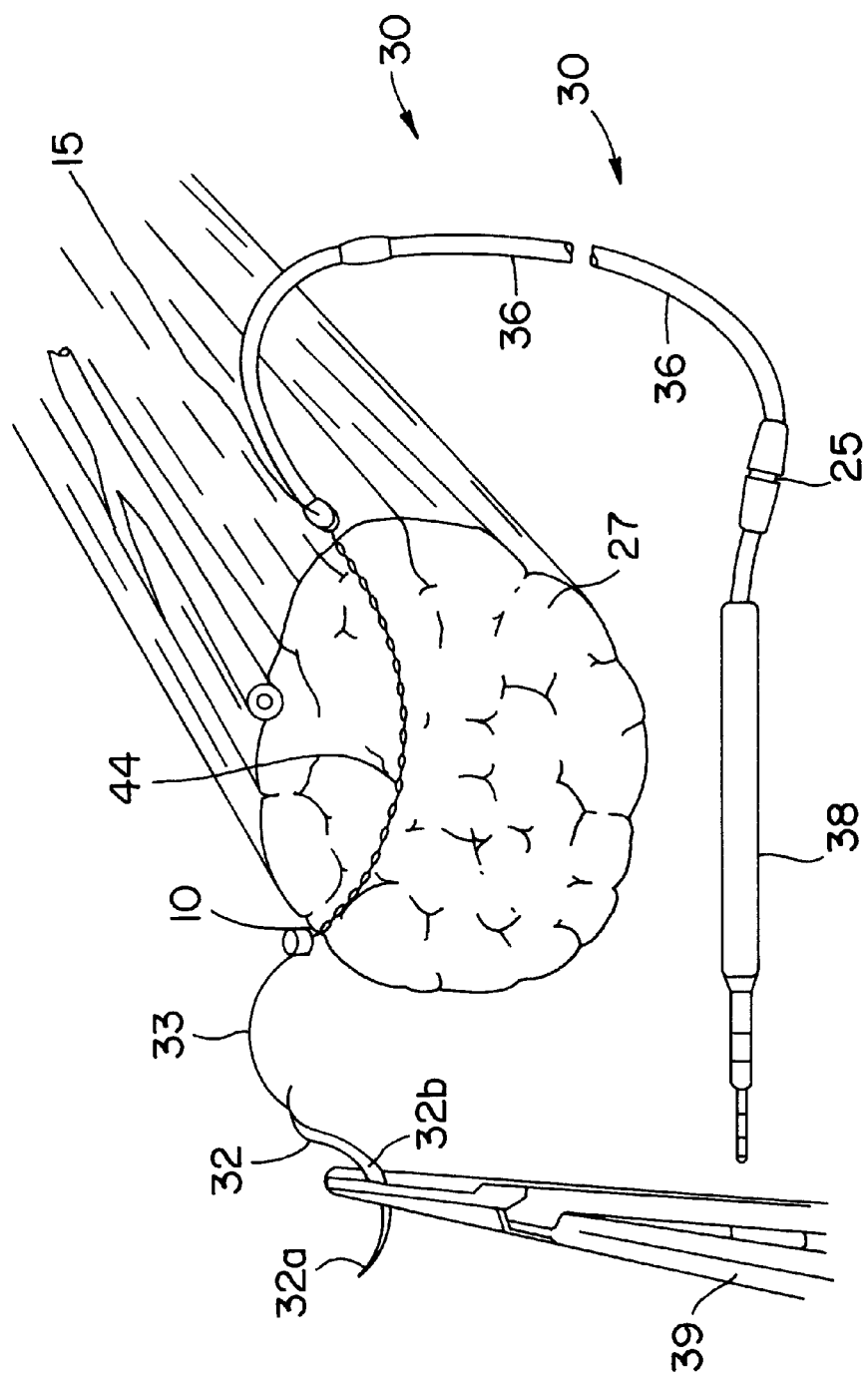
FIG. 3 shows a cross-sectional view of one embodiment of an intramuscular lead of the present invention implanted in muscle tissue.

Referring now to FIG. 3, there is shown a cross-sectional view of patient's muscle tissue 27 having one embodiment of lead 30 of the present invention disposed therein. Scissors 39 are employed by a physician to grip portions of needle 32 and draw electrode 44 through and into a desired portion of muscle tissue 27. Proximal fixation member 15 prevents or impedes pulling lead body 36 into muscle tissue 27. In similar fashion, distal fixation member 10 (once in place) prevents portions of electrode 44 from moving outside muscle tissue 27 in the proximal direction. Optional anchoring sleeve 25 may be employed to appropriately locate or position lead body 36 in a desired location.

In preferred embodiments of the present invention, lead 30 is configured to provide satisfactory stimulation thresholds for appropriate muscle contraction of muscle tissue 27. Needle 32 is appropriately shaped and of appropriate length to provide optimum results. The length of lead 30 should be sufficient to provide adequate slack in lead body 36 to permit bi-lateral implants. Moreover, in a preferred embodiment of the present invention proximal and distal affixation members 15 and 10, respectively, optionally include structures for suturing or anchoring same to muscle tissue 27 once electrode 44 has been appropriately positioned within same. It is also desired that at least portions of lead 30 be visible using x-ray imaging techniques.

Figure 4:
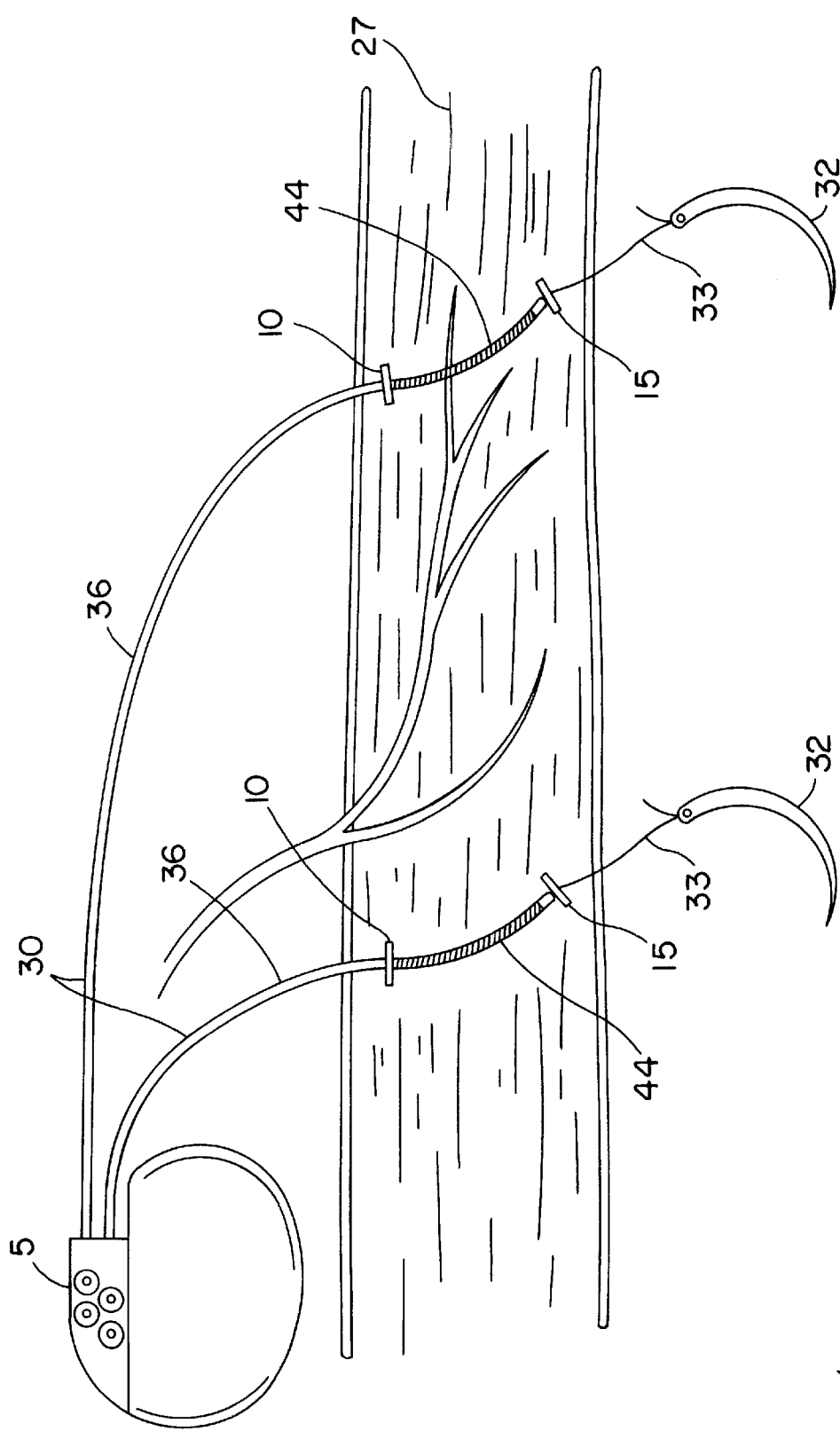
FIG. 4 shows two embodiments of an intramuscular medical lead of the present invention implanted within muscle tissue and connected to an implantable electrical stimulator.

Referring now to FIG. 4, there is shown intramuscular stimulating system 3 comprising IPG 5 and two leads 30 appropriately implanted in intramuscular tissue 27 such that electrodes 44 thereof provide appropriate electrical stimulation to tissue 27. Curved needles 32 of lead 30 are removed by the physician once distal affixation member 10 has been placed or located at or near the distal end of electrodes 44. In a preferred embodiment of the present invention, electrode 44 is about 25 mm in length, although other electrode lengths are contemplated in the present invention including, but not limited to, about 5 mm, about 10 mm, about 15 mm, about 20 mm, about 25 mm, about 30 mm, about 35 mm and about 40 mm.

Figure 5:
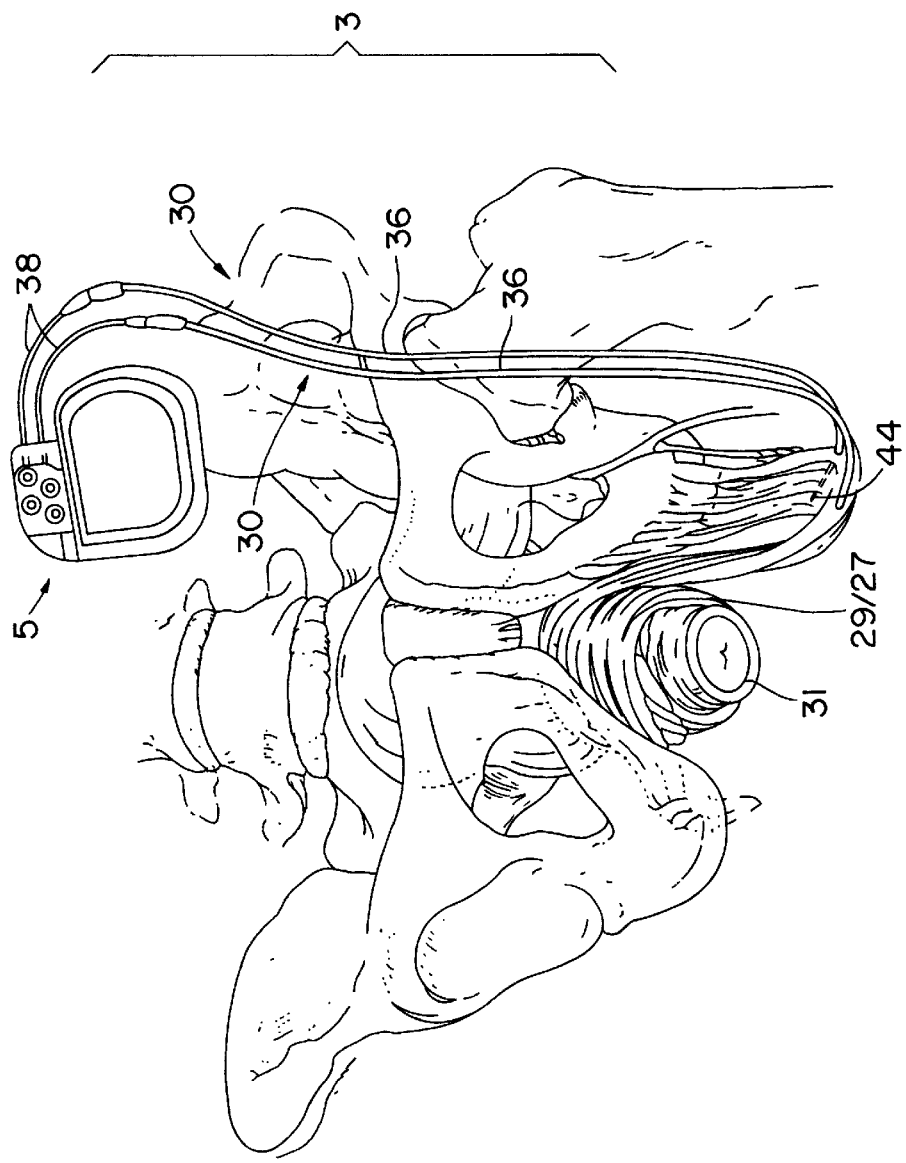
FIG. 5 shows a perspective view of a one embodiment of an intramuscular medical electrical lead and corresponding electrical stimulator implanted within the human body in accordance with a dynamic graciloplasty surgical procedure.

FIG. 5 shows intramuscular stimulating system 3 comprising IPG 5 and leads 30. IPG 5 may be, for example, a Medtronic Model No. 3023 Interstim IPG. Such an IPG may be programmed using a Medtronic Model No. 3031 Patient Programmer. In the embodiment of system 3 of the present invention illustrated in FIG. 5, a gracilis muscle 29/27 is wrapped around portions of anus 31. Gracilis muscle 29/27 is then electrically stimulated through means of electrodes 44 implanted therewithin, such electrodes being electrically connected to IPG 5. The configuration of gracilis muscle 29/27 illustrated in FIG. 5 is known as a dynamic graciloplasty procedure.

Figure 6A:
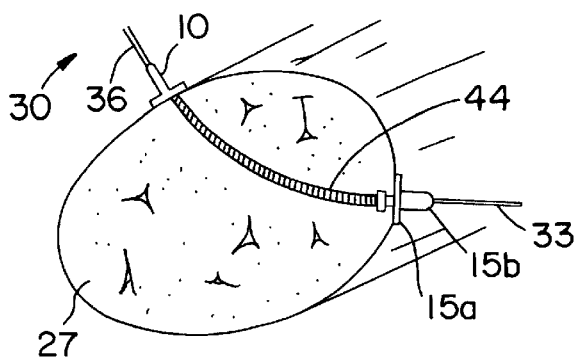
FIG. 6(a) shows disk trumpet-and/or disk-shaped embodiments of the distal and proximal fixation members of the present invention.
Figure 6B:
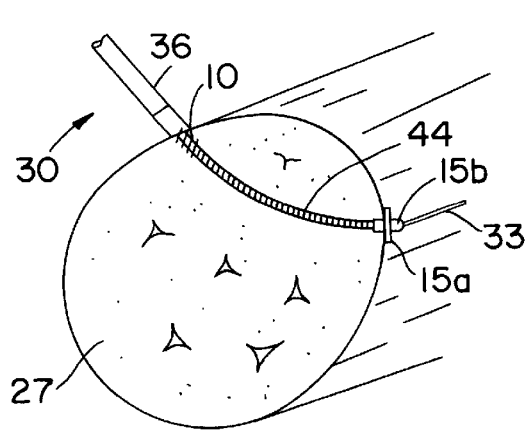
FIG. 6(b) shows helical screw-and/or cone-shaped embodiments of the distal and proximal fixation members of the present invention.
Figure 6C:
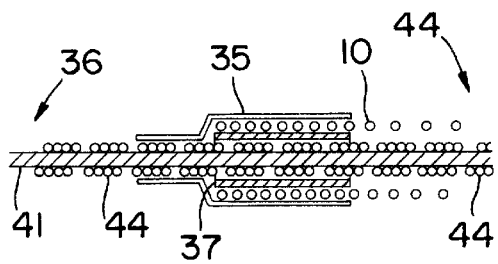
FIG. 6(c) shows a cross-sectional view of the helical screw-shaped embodiment of the proximal fixation member illustrated in FIG. 6(b)

FIGS. 6(a) through 6(c) illustrate various embodiments of the proximal and distal fixation members of the present invention. In FIG. 6(a), electrode 44 is positioned within muscle 27, and is secured reliably and relatively fixedly therein through means of proximal and distal affixation members 10 and 15, respectively. As shown in FIG. 6(a), proximal fixation member may form a toroid-shaped member fabricated most preferably from silicon rubber. Distal fixation member 15 is shown as comprising snap-on disk 15a having a central hole disposed therethrough through which line 33 is threaded, snap-on disk then being pushed over distal cone or member 15b for frictional engagement thereof. It is contemplated in the present invention that any of the proximal and distal fixation members 10 and 15 illustrated in any of the Figures hereof may be positionally switched. In FIG. 6(b), proximal fixation member 10 is of the helical screw-in type. Distal fixation member 15 again comprises cone 15b and snap-on disk 15a. FIG. 6(c) shows a cross-sectional view of portions of lead 30 in the vicinity of screw-in fixation member 10 in FIG. 6(b). Crimp sleeve 65 slides over helical screw 10 and crimps same to electrical conductor 41 and electrode 44. Electrical insulation 37 may be disposed between helical screw-in member 10 and electrode 44.

Figure 6D:
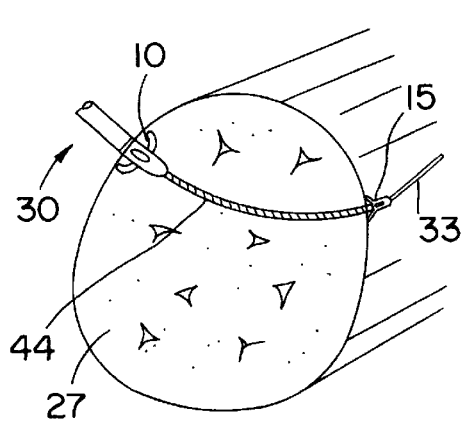
FIG. 6(d) shows tine-shaped embodiments of the distal and proximal fixation members of the present invention.
Figure 6E:
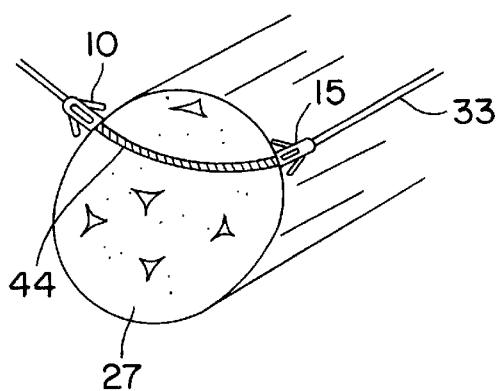
FIG. 6(e) shows further embodiments of tine-shaped embodiments of the distal and proximal fixation members of the present invention.

FIG. 6(d) illustrates yet another embodiment of the present invention, where proximal and distal fixation members 10 and 15 comprise tined members that prevent or inhibit movement of electrode 44 following implantation within muscle tissue 27. Tines attached to fixation member 10 in FIG. 6(d) project proximally and inhibit movement of electrode 44 in the proximal direction. Contrariwise, in the embodiment of the present invention illustrated in FIG. 6(d) tines attached to proximal fixation member 10 prevent or inhibit movement of electrode 44 in the distal direction.

Figure 7A:
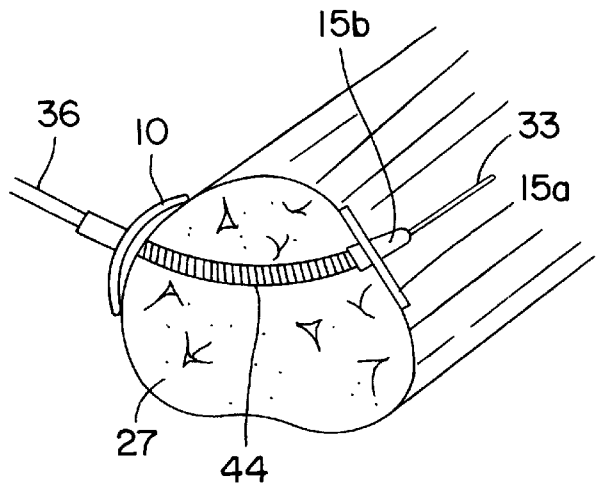
FIG. 7(a) shows a cross-sectional view of one embodiment of a variable length and flexibility electrode implanted within human muscle tissue.

FIG. 7(a) illustrates muscle tissue 27 in cross-section having yet another embodiment of the lead of the present invention implanted therein. Disk-shaped proximal fixation member 10 prevents electrode 44 from moving in the distal direction, while similarly-shaped distal fixation member 15 prevents movement of electrode 44 in the proximal direction once electrode 44 has been appropriately positioned within muscle tissue 27. In the embodiment of the present invention shown in FIG. 7(a), distal fixation member 15 most preferably comprises circular disk 15b having a central hole disposed therethrough through which line 33 is threaded, the hole being dimensioned and configured to snappingly engage a rim or groove disposed in cone 15b.

Figure 7B:
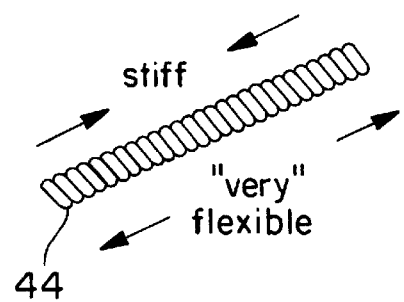
FIG. 7(b) illustrates the mechanical principles involved in varying the flexibility of the electrode illustrated in FIG. 7(a)

As shown in FIG. 7(a) and 7(b), an alternative embodiment of electrode 44 comprises relatively tightly wound electrode wire which is capable of being pulled apart to thereby elongate electrode 44 and to increase the flexibility thereof. Additionally, electrode 44 may also be shaped such that spaces are initially disposed between adjoining windings thereof. In such an embodiment of the present invention, those windings may be pushed together to increase the stiffness of electrode 44 or pulled apart to increase the flexibility thereof.

Figure 7C:
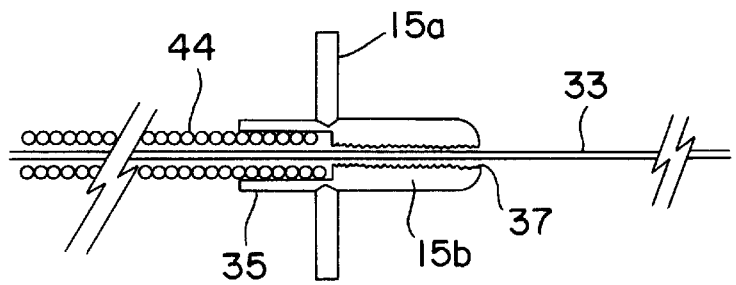
FIG. 7(c) shows one embodiment of the electrode of FIG. 7(a) in cross-section in the region of the distal portion thereof.
Figure 7D:
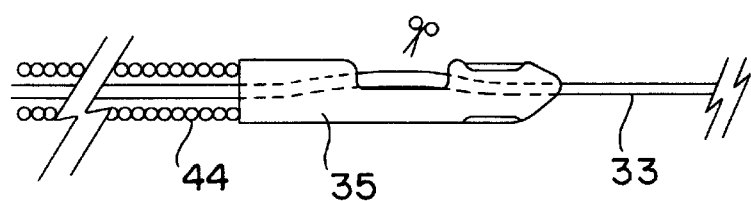
FIG. 7(d) shows yet another embodiment of the electrode of FIG. 7(a) in cross-section in the region of the distal portion thereof.

Referring now to FIGS. 7(c) and 7(d) there are shown two different embodiments for securing wound electrode 44 illustrated in FIGS. 7(a) and 7(b) to distal portions of lead 30. Cone-shaped member 15b may be configured to crimpingly engage distal portions of wound electrode 44 in the region of sleeve 35. Alternatively, crimp sleeve 35 may be configured such that portions of lead 30 disposed distally therefrom may be separated from lead 30 using surgical scissors or mechanical breaking or snapping of a weakened zone.

The present invention includes within its scope methods of implanting, using and making the leads described hereinabove. For example, the invention includes a method for implanting an intramuscular lead having distal and proximal ends, the lead being suitable for electrical stimulation or sensing of muscle tissue and comprising at least one stimulating and/or sensing electrode, the lead further comprising at least one of a proximal fixation member located proximally from the electrode and a distal fixation member located distally from the electrode, the method comprising: (a) positioning the at least one electrode in electrical contact with at least a portion of muscle tissue, the electrode being electrically connected to at least one electrical conductor, the conductor having a proximal end connected electrically to a proximal connector, the connector being configured for attachment to an external electrical apparatus; (b) securing the electrode to the at least portion of the muscle tissue; and (c) positioning at least one of the proximal fixation member and the distal fixation member in or on the muscle tissue to prevent or inhibit movement or relocation of the at least one electrode in the distal or proximal directions.

The Figures show disk-shaped tined, trumpet-shaped, sleeve-shaped, cone-shaped, and helical screw proximal and distal fixation members 10 and 15, respectively, but any suitably shaped or configured fixation member, whether proximal or distal, may be employed. The fixation member may be formed of polyurethane, silicon rubber, medical grade plastic, suitable biocompatible polymers, stainless steel or any other suitable biocompatible, biostable material. Additionally, either or both of the proximal and distal fixation members may be fixedly attached to regions near the proximal and distal ends of the electrode, respectively, or may be attachable to such regions after the electrode has been implanted in the muscle tissue at the desired site. For example, a fixation member may assume a split disk configuration or shape having two portions which snap together when closed upon one another, where the two portions are opened for placement around the lead body, electrode crimping sleeve, cone-shaped member or the electrode, and are then closed therearound by snapping the two portions together. As discussed above, one of the fixation members may slide onto the line or member 33, and then be moved in the distal or proximal directions into a position where the fixation member snappingly or otherwise engages at least portions of a locking member or cone to thereby be secured into position.

It is also not a requirement of the present invention that the fixation members be located precisely "at" the proximal or distal end of the electrode. Instead, either fixation member may be attached, by way of example only, to a location disposed proximally or distally from the electrode, to a location on the lead body disposed distally from the electrode, to a location disposed proximally from the electrode, to member 33, or even to other members or portions of lead 10. What is important is that the electrode be reliably and relatively fixedly positioned within the muscle tissue at a desired site through means of the one or more fixation members, and that such positioning of the electrode be so maintained over a desired period of time.

Line or member 33 need not be electrically non-conductive, and may be formed integrally with, by way of example only, electrode 44 or lead body 36. Line or member 33 may also include a coil affixation member, such as a pigtail, therein.

Since the connectors of the present invention are required to be in electrical contact with the electrical conductors of lead 30, the conductors are preferably attached to the distal ends of the connectors by a combination of compressing, inserting and crimping steps. Other methods of electrically conductive attachment such as brazing, soldering or welding may of course be utilized. The connectors of the present invention are not limited to pin connectors, but include any plurality of connectors having suitable configurations for attachment to the blunt end. The proximal ends of the connectors need not be removed from the needle by manual means only. Specially configured tools may be used to break or pull the connectors free of the needle.

Furthermore, the present invention is not limited to embodiments where all electrodes are attached to the same lead body, where one electrode must necessarily be disposed proximally or distally of the other electrode or electrodes, or where the electrodes are crimpingly attached to the conductors. For example, an electrode of the present invention may be formed by merely stripping away insulation overlying bare wire at a suitable location, by attaching a clip to bare wire, or by heat shrinking electrically conductive heat shrink over selected portions of bare wire.

The scope of the present invention is not limited to intramuscular electrical stimulation or sensing applications, but extends to neural, defibrillation, cardiac mapping, abdominal stimulation, and other medical and medical device applications and methods. Moreover, lead 30 of the present invention may be employed at numerous different muscle implant locations, and is not limited to use in cardiomyoplasty or gracilopasty applications. For example, lead 30 of the present invention may be employed in gluteus muscle implantation procedures to correct fecal or urinary incontinence, and may further be employed in rectal muscle implants in bladder myoplasty procedures. The scope of the present invention is not limited to applications where a human organ or plurality of organs is sensed, monitored, paced, or defibrillated, but includes similar applications in animals.

The present invention also includes within its scope methods of making the leads, electrodes, and fixation members disclosed hereinabove.

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents, patent applications and/or printed publications disclosed hereinabove are hereby incorporated into the specification hereof, each in its respective entirety.

We claim:

1. An elongated medical lead having distal and proximal ends, the lead being suitable for at least one of electrically stimulating and sensing electrical signals originating in at least a portion of human or animal muscle tissue, comprising:
   (a) a lead body having distal and proximal ends, the lead body comprising at least one electrical conductor;
   (b) at least one electrical conductor disposed at least partially within the lead body;
   (c) at least one electrode electrically connected to the electrical conductor, the electrode having proximal and distal ends;
   (d) at least one of a proximal fixation member and a distal fixation member, the proximal fixation member being located near or attachable to a first position located near the proximal end of the electrode, the distal fixation member being located near or attachable to a second position located near the distal end of the electrode; and
   (e) a distal line having proximal and distal ends, the proximal end of the distal line being connected to the lead body at a location distal from the distal end of the electrode;

wherein the electrode forms a variable-stiffness member whose flexibility is adapted to be changed by a physician.

2. An implantable system for electrically stimulating or sensing electrical signals originating in at least a portion of human or animal muscle tissue, comprising:
   (a) an implantable pulse generator for providing electrical stimulation signals and/or receiving sensed electrical signals;
   (b) an elongated medical lead having distal and proximal ends, the the proximal end of the lead being configured for attachment to the implantable pulse generator, the lead being suitable for at least one of electrically stimulating and sensing electrical signals originating in at least a portion of the human or animal muscle tissue, the lead comprising;
      (i) a lead body having distal and proximal ends, the lead body comprising at least one electrical conductor;
      (ii) at least one electrical conductor disposed at least partially within the lead body;
      (v) at least one electrode electrically connected to the electrical conductor, the electrode having proximal and distal ends;
      (vi) at least one of a proximal fixation member and a distal fixation member, the proximal fixation member being located near or attachable to a first position located near the proximal end of the electrode, the distal fixation member being located near or attachable to a second position located near the distal end of the electrode; and
      (v) a distal line having proximal and distal ends, the proximal end of the distal line being connected to the lead body at a location distal from the distal end of the electrode;

wherein the electrode forms a variable-stiffness member whose flexibility is adapted to be changed by a physician.

* * * * *